(12) United States Patent
Hale et al.

(10) Patent No.: US 8,321,196 B2
(45) Date of Patent: Nov. 27, 2012

(54) SYSTEM AND METHOD FOR GENERATING RADIOLOGICAL PROSE TEXT UTILIZING RADIOLOGICAL PROSE TEXT DEFINITION ONTOLOGY

(75) Inventors: Charles R. Hale, Trumbull, CT (US); Yihong Ding, Westport, CT (US)

(73) Assignee: FUJIFILM Medical Systems USA, Inc., Stamford, CT (US)

( * ) Notice: Subject to any disclaimer, the term of this patent is extended or adjusted under 35 U.S.C. 154(b) by 352 days.

(21) Appl. No.: 12/572,602

(22) Filed: Oct. 2, 2009

(65) Prior Publication Data

US 2011/0035206 A1    Feb. 10, 2011

Related U.S. Application Data

(63) Continuation-in-part of application No. 12/535,825, filed on Aug. 5, 2009.

(51) Int. Cl.
*G06F 17/28*    (2006.01)
(52) U.S. Cl. ............................................................ 704/2
(58) Field of Classification Search .................... 704/2
See application file for complete search history.

(56) References Cited

U.S. PATENT DOCUMENTS

| | | |
|---|---|---|
| 6,526,415 B2 | 2/2003 | Smith et al. |
| 6,654,731 B1 | 11/2003 | Mahesh |
| 7,020,326 B1 | 3/2006 | Hsu |
| 7,136,852 B1 | 11/2006 | Sterling et al. |
| 7,209,923 B1 | 4/2007 | Cooper |
| 7,260,480 B1 | 8/2007 | Brown et al. |
| 7,289,651 B2 | 10/2007 | Vining et al. |
| 7,421,647 B2 | 9/2008 | Reiner |
| 7,493,253 B1 | 2/2009 | Ceusters et al. |
| 7,505,989 B2 | 3/2009 | Gardner et al. |
| 7,512,575 B2 | 3/2009 | Mahesh |
| 7,512,576 B1 | 3/2009 | Syeda-Mahmood et al. |
| 7,542,969 B1 | 6/2009 | Rappaport et al. |
| 7,908,293 B2 | 3/2011 | Aronson et al. |
| 8,046,226 B2 | 10/2011 | Soble et al. |
| 2002/0046062 A1 | 4/2002 | Kameda |

(Continued)

FOREIGN PATENT DOCUMENTS

JP    11066197    3/1999

(Continued)

OTHER PUBLICATIONS

Biolchini, Jorge, "Developing a UMLS-based Ontology of Cardiology Procedures for Cognitive Support in Medical Decision Making,"Lister Hill Nat'l Ctr.,Nat'l Lib. Med., Apr. 4, 2002.

(Continued)

*Primary Examiner* — Jakieda Jackson
(74) *Attorney, Agent, or Firm* — Woods Oviatt Gilman LLP

(57) ABSTRACT

The present invention is generally directed to a method programmed in a computing environment for providing prose text reporting, utilizing a prose text definition ontology comprising linguistic knowledge and a base report domain ontology. A system and method are provided to define various aspects of radiological report information processing as concept properties represented by a vocabulary of one or more instances of ontology concepts and presented in prose text. Even further, a system and method are provided for consulting a radiological prose text definition ontology wherein radiological domain concepts and relationships may be expressed or further utilized by other application programs. Users are able to quickly, accurately and consistently consult and report radiological observations in unambiguous prose text.

5 Claims, 8 Drawing Sheets

U.S. PATENT DOCUMENTS

| | | | |
|---|---|---|---|
| 2004/0125131 | A1 | 7/2004 | Phelps |
| 2005/0170323 | A1 | 8/2005 | Jarrell et al. |
| 2005/0182657 | A1 | 8/2005 | Abraham-Fuchs et al. |
| 2006/0100738 | A1 | 5/2006 | Alsafadi et al. |
| 2006/0143046 | A1 | 6/2006 | Kawakami et al. |
| 2006/0265249 | A1 | 11/2006 | Follis et al. |
| 2006/0271556 | A1 | 11/2006 | Mukherjee et al. |
| 2007/0005621 | A1 | 1/2007 | Lesh et al. |
| 2007/0027636 | A1 | 2/2007 | Rabinowitz |
| 2007/0055552 | A1 | 3/2007 | St. Clair et al. |
| 2007/0094188 | A1 | 4/2007 | Pandya et al. |
| 2007/0198250 | A1 | 8/2007 | Mardini |
| 2008/0027889 | A1 | 1/2008 | Zhou et al. |
| 2008/0037852 | A1 | 2/2008 | Zhou et al. |
| 2008/0052126 | A1 | 2/2008 | Sasai et al. |
| 2008/0059391 | A1 | 3/2008 | Rosales et al. |
| 2008/0201172 | A1 | 8/2008 | McNamar |
| 2008/0201280 | A1 | 8/2008 | Martin et al. |
| 2008/0208631 | A1 | 8/2008 | Morita et al. |
| 2008/0243548 | A1 | 10/2008 | Cafer |
| 2008/0244453 | A1 | 10/2008 | Cafer |
| 2008/0270120 | A1* | 10/2008 | Pestian et al. .................. 704/9 |
| 2008/0294459 | A1 | 11/2008 | Angell et al. |
| 2008/0312961 | A1 | 12/2008 | Alsafadi |
| 2009/0006467 | A1 | 1/2009 | Visscher |
| 2009/0018867 | A1 | 1/2009 | Reiner |
| 2009/0030731 | A1 | 1/2009 | Reiner |
| 2009/0037220 | A1 | 2/2009 | Chambers et al. |
| 2009/0055378 | A1 | 2/2009 | Alecu et al. |
| 2009/0076839 | A1 | 3/2009 | Abraham-Fuchs et al. |
| 2009/0099862 | A1 | 4/2009 | Fireman et al. |
| 2009/0132285 | A1 | 5/2009 | Jakobovits |
| 2009/0192800 | A1* | 7/2009 | Brandt ...................... 704/270.1 |
| 2009/0222286 | A1 | 9/2009 | Elsholz |
| 2009/0228299 | A1* | 9/2009 | Kangarloo et al. ............... 705/2 |
| 2010/0063799 | A1* | 3/2010 | Jamieson ......................... 704/9 |
| 2010/0131883 | A1 | 5/2010 | Linthicum et al. |
| 2010/0138231 | A1 | 6/2010 | Linthicum et al. |
| 2010/0145720 | A1 | 6/2010 | Reiner |
| 2010/0293164 | A1 | 11/2010 | Weese et al. |

FOREIGN PATENT DOCUMENTS

| | | |
|---|---|---|
| JP | 2001118008 | 4/2001 |
| JP | 2003122849 | 4/2003 |
| JP | 2004005565 | 1/2004 |
| JP | 2007304661 | 11/2007 |
| JP | 2008021015 | 1/2008 |
| JP | 2008192002 | 8/2008 |
| JP | 2008250747 | 10/2008 |
| JP | 2008250748 | 10/2008 |
| WO | WO 2007/024617 | 3/2007 |
| WO | WO 2008/115449 | 9/2008 |

OTHER PUBLICATIONS

Galanis, Dimitrios, et al, "An Open-Source Natural Language Generator for OWL Ontologies and its Use in Protege and Second Life," Athens University of Econ/Bus., Athens Greece.

Azad, Abul K., "Non-Final Office Action," for U.S. Appl. No. 12/625,880, filed Nov. 25, 2009, mailed Sep. 28, 2012, Alexandria, Virginia.

Wennerberg, et al., KEMM: A Knowledge Engineering Methodology in the Medical Domain, Proc of the 5th International Conference on Formal Ontology in Information Systems (FOIS). Saarbruecken, Germany, Jun. 19, 2008, pp. 1-13.

Achour, et al, A UMLS based Knowledge Acquisition Tool for Rule-based Clinical Decision Support System Development, Journal of the American Medical Informatics Association vol. 8 No. 4 Jul./Aug. 2001, pp. 351-360.

Jannin, et al., Model for defining and reporting Reference-based Validation Protocols in Medical Image Processing, Int. Journ. Comput. Assisted Radio and Surg. 2006, pp. 1-26.

Winston III, Edward B., "Non-Final Office Action," for U.S. Appl. No. 12/556,923, filed Sep. 10, 2009, mailed Dec. 9, 2011, Alexandria, Virginia.

Fernandez Rivas, Omar F., "Non-Final Office Action," for U.S. Appl. No. 12/587,174, filed Oct. 2, 2009, mailed Mar. 29, 2012, Alexandria, Virginia.

Marwede et al ("RadiO: A Prototype Application Ontology for Radiology Reporting Tasks" AMIA 2007).

Zhou et al ("Semantics and CBIR: A Medical Imaging Perspective" Jul. 2008).

Daniel Rubin ("Creating and Curating a Terminology for Radiology: Ontology Modeling and Analysis" 2008).

Gangemi et al ("Modeling Ontology Evaluation and Validation" 2006).

Wong, Lut, "Non-Final Office Action," for U.S. Appl. No. 12/535,825, filed Aug. 5, 2009, mailed Mar. 26, 2012, Alexandria, Virginia.

Rubin, Daniel L, et al, "Protege: A Tool for Managing and Using Terminology in Radiology Applications," Journal of Digital Imaging, vol. 0, No. 0, 2007: pp. 1-13.

Biolchini, Jorge,"Developing a UMLS-based Ontology of Cardiology Procedures for Cognitive Support in Medical Decision Making,"Lister Hill Nat'l Ctr.,Nat'l Lib. Med., Apr. 4, 2002.

Baneyx, Audrey, et al, "Methodology to Build Medical Ontology from Textual Resources," AMIA Annu. Symp. Proc. 2006; 2006: 21-25.

Galanis, Dimitrios, et al, "An Open-Source Natural Language Generator for OWL Ontologies and its Use in Protege and Second Life," Athens University of Econ/Bus., Athens Greece, 2009.

* cited by examiner

SYSTEM AND METHOD FOR GENERATING RADIOLOGICAL PROSE TEXT UTILIZING RADIOLOGICAL PROSE TEXT DEFINITION ONTOLOGY

CROSS REFERENCE TO RELATED APPLICATIONS

This application is a continuation-in-part of prior U.S. patent application Ser. No. 12/535,825, filed Aug. 5, 2009. The content of U.S. patent application Ser. No. 12/535,825 is hereby incorporated by reference in its entirety.

TECHNICAL FIELD

The present invention is directed in general to imaging technologies and more particularly to medical imaging and Picture Archiving and Communication Systems (PACS) having an image display wherein the identification, validation and classification of radiological information is desired, and more importantly, that the reporting of radiological information conforms to this paradigm and is presented in a consistent and unambiguous manner. A system and method are provided to define various aspects of radiological report information processing as concept properties represented by a vocabulary of one or more instances of ontology concepts and presented in prose text. Even further, a system and method are provided for consulting a radiological prose text definition ontology wherein radiological domain concepts and relationships may be expressed or further utilized by other application programs. Users are able to quickly, accurately and consistently consult and report radiological observations in unambiguous prose text.

BACKGROUND OF THE INVENTION

In medical imaging, Picture Archiving and Communication Systems (PACS) are a combination of computers and/or networks dedicated to the storage, retrieval, presentation and distribution of images. While images may be stored in a variety of formats, the most common format for image storage within the PACS system is Digital Imaging and Communications in Medicine (DICOM). DICOM is a standard in which radiographic images and associated meta-data are communicated to the PACS system from imaging modalities for interaction by end-user medical personnel.

Medical personnel spend a significant amount of their time addressing administrative tasks. Such tasks include, for example, documenting patient interaction and treatment plans, preparing billing, reviewing lab results, recording observations, and preparing reports for health insurance. Time spent on performing such tasks diminish the time available for patients, and in some instances, lead to inaccurate and hastily compiled reports or records when personnel are faced with the need to see multiple patients.

In order to address time deficiency issues, the current trend in the medical field is to automate as many health care related processes as possible by leveraging various technologies, and thereby freeing up personnel to spend more time with patients rather than performing administrative tasks. Another objective in this arena is to ensure that when administrative tasks are performed, they are accomplished in an accurate and consistent manner. One approach to achieving this objective is to provide a standardized representation for healthcare related data, particularly within the various specialty areas, such as radiology, cardiology, etc.

Health care data is not easily reusable by disparate groups in the radiological field because it is stored with different methods and in different formats across a wide range of information technology. Various initiatives by groups and organizations across the globe, including the National Institutes of Health, Food and Drug Administration, and other medical bodies, have driven a set of standards for the consolidation of medical information into a common framework. One such standard is RadLex, which is a standard radiological lexicon proposed by the Radiological Society of North America, for uniform indexing and retrieval of radiology information. RadLex is a taxonomy having class hierarchies. RadLex functions essentially as a dictionary of terms and the notes relationships among the terms. RadLex has some crucial limitations. The most significant of these limitations is the inability to support radiological findings and the relationships between the findings and the characteristics of the findings. What is needed is an extension to RadLex—an extension that provides domain specific modeling, which can then be applied to or utilized by a wide variety of applications such as report tools, treatment analysis programs, tools for classification and verification of radiological information, and systems for improving radiological work flow. Such an extension would utilize an ontology that is domain specific to process and express radiological information.

Ontology is a data model for the modeling of concepts and the relationships between a set of concepts. Ontologies are utilized to illustrate the interaction between the set of concepts and corresponding relationships within a specific domain of interest. Thus, the concepts and the relationships between the concepts can be represented in readable text, wherein descriptions are provided to describe the concepts within a specific domain and the relationship axioms that constrain the interpretation of the domain specific concepts.

Numerous current products and research efforts offer tools that streamline data integration. These include centralized database projects such as the Functional Magnetic Resonance Imaging Data Center and the Protein Data Bank, distributed data collaboration networks such as the Biomedical Informatics Research Network, commercial tools for data organization, and systems for aggregating healthcare information such as Oracle Healthcare Transaction Base. In addition, tools have been developed to automatically validate data integrated into a common framework. Validation calls for techniques such as declarative interfaces between the ontology and the data source and Bayesian reasoning to incorporate prior expert knowledge about the reliability of each source.

While automated data integration and validation require fewer human resources, they necessitate that data have well-defined a priori structure and meaning.

There are a number of functionalities not provided by the systems described earlier. Accordingly, there is a need for a comprehensive system which is capable of enabling researchers to: 1) efficiently enter heterogeneous local data into the framework of the Unified Medical Language System (UMLS) based ontology; 2) make necessary extensions to the standardized ontology to accommodate local data; 3) validate the integrated data using expert rules and statistical models defined in the data classes of the standardized ontology; 4) efficiently upgrade data that fails validation; 5) leverage the integrated data for reporting functionality and predictions; and 6) express the integrated data unambiguously as prose text. This is particularly the case in the field of radiology, and even more specifically within the various domains therein such as mammography.

To overcome some of the deficiencies earlier described, some existing systems have attempted to minimize the amount of effort that may be required to report and express radiological findings. However, these systems suffer from a myriad of drawbacks. Essentially these solutions have a non-standard library or vocabulary, no error, terminology, or consistency checking, and no collaboration or tool that can be used by other application programs.

The shortcomings of the prior art are overcome and additional advantages are provided through the provision of a method for utilizing ontology that is based upon data obtained from unstructured and semi-structured knowledge sources to provide identification, validation and classification of radiological report concepts and to express those concepts as prose text.

The present invention addresses these needs as well as other needs.

SUMMARY OF THE INVENTION

The present invention is directed in general to a system and method that employs radiological prose text definition ontology to specify and model radiological prose text conversation information as knowledge. The present invention provides a methodology to consult the conversation domain ontology and provide prose text report information. The prose text report information is provided in reference to a subject patient and expresses the radiological domain concepts and relationships involved in the consultation. The method comprises defining one or more aspects of radiology reports as concept properties represented by a vocabulary of one or more instances of the radiological report domain ontology and converting those concept properties into prose text using radiological prose text definition ontology.

The radiological prose text definition ontology declares and fulfills a model of linguistic knowledge and radiological domain knowledge by employing a context that defines a set of radiological knowledge and the relationships among said set of linguistic knowledge with respect to imaging modalities when necessary or appropriate. The invention validates that an information item of interest relating to a subject patient or imaging modalities is radiological in nature and resides in the domain knowledge. The invention further identifies a definitive concept of said information item from within said radiological domain of knowledge and classifies the information item as an object with properties. The object's properties represent relationships among said findings and finding characteristics or concepts. The invention then expresses the definitive concepts and relationships as prose text.

Exemplary embodiments of the present invention relate to a solution for the extraction of information from unstructured knowledge sources of radiological report information and non-radiological knowledge sources, and further processing of the derived information by linguistic formatting ontology.

BRIEF DESCRIPTION OF THE DRAWINGS

The above-mentioned features and other features and advantages of this invention, and the manner of attaining them, will become apparent and be better understood by reference to the following description of the invention in conjunction with the accompanying drawing, wherein.

DETAILED DESCRIPTION OF THE INVENTION

Figure 1:
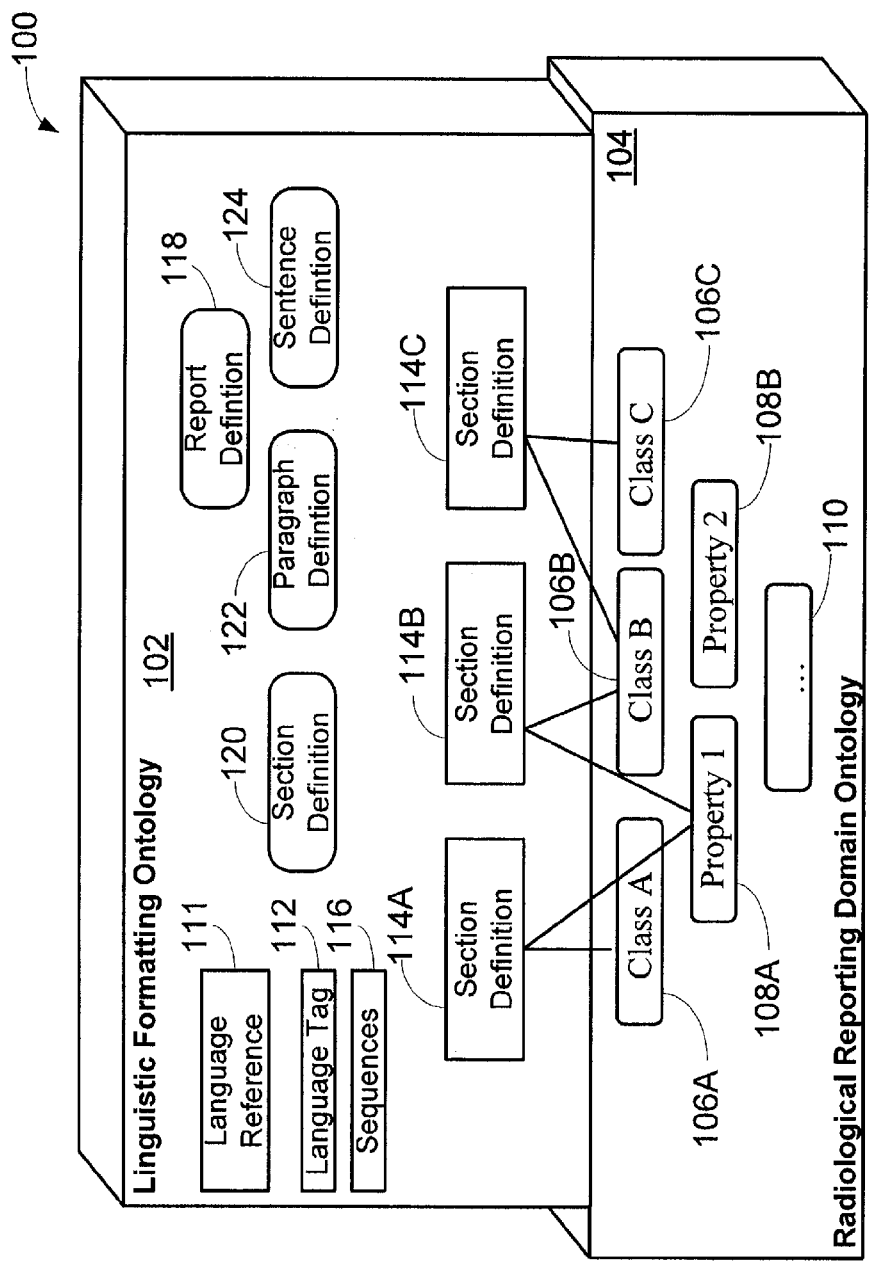
FIG. 1 is an illustrative block diagram of a prose text definition ontology comprising a linguistic formatting ontology and a radiological reporting domain ontology.

The disclosed embodiments are intended to be illustrative since numerous modifications and variations thereof will be apparent to those of ordinary skill in the art.

This document provides an overview of the techniques and implementation necessary to provide a consistency of terminology and unambiguous prose text in radiological reporting in accordance with the present invention. An exemplary implementation of particular features of the present invention for modeling radiological prose text conversation information as knowledge is discussed. Following this, other aspects of the invention as they pertain to the use and function of the invention are discussed. Finally, an exemplary computer environment for the implementation and use of the invention is described.

The present invention employs radiological prose text definition ontology to specify and model radiological prose text conversation information as knowledge. A system and method are provided to allow for consulting the ontology in the context of the model that the ontology fulfills. Consulting the ontology results in prose text that properly and unambiguously expresses radiological domain concepts and relationships that are provided in the consultation. The concepts and relationships are initially identified, validated and classified as radiological report information by consulting a radiological report domain ontology the details of which are discussed in the previously identified U.S. patent application Ser. No. 12/535,825, The present invention relates to a solution for the conversion of radiological report domain ontology concepts and relationships into prose text using a radiological prose text definition ontology. A set of subject-matter specific relationships are established as a logical foundation for the ontological subject matter domain. The subject-matter specific relationships can be derived partially from a pre-existing information source (e.g., RadLex, the radiological lexicon), other ontology, and partially from the knowledge that needs to be modeled for an identified subject. For example, ontology on the subject of mammography will use lumps or masses as topic concepts. The relationships modeled in the ontology may correspond to disease-specific relationships such as biopsy, additional exam, symptoms, location, further treatments, etc. In another example, a report may utilize clinical indications as a concept. In this instance a relationship may correspond to a specific imported ontology that provides a knowledge source, such as anatomic location ontology, follow-up procedure ontology, etc. Once the subject-matter specific relationships have been established, semantics for linguistic connectors and sequences are specified. The semantics facilitate the modeling of informational items that are associated with respective objects within the knowledge source. The information items that are identified within the knowledge source correspond to predetermined subject-matter specific relationships.

The present invention utilizes ontology to define a set of knowledge and relationships among the knowledge thereby employing a context. For example, if there is a finding of a tumorous mass in an image, the system knows what other information would be relevant to that finding such as size, density, location and other characteristics that apply to that finding, as well as the relationships between the findings and finding characteristics. The set of knowledge includes other specific ontology and is then applied when a report is being constructed.

Ontological models are used to talk about "things." An important vocabulary tool is "relations" between things. An ontology model itself does not include the "things," but introduces classes and relations, which can then be used as a vocabulary for talking about and classifying things. In the field of medicine, ontology is used in solving problems in the field of medical terminology, including the organization of copious amounts of data, the alignment and integration of heterogeneous knowledge, and disambiguates in terminology.

The present invention provides a combination of an intelligent database and system, which can provide not only stored information, but also information which can be determined or derived by knowledge of the technical domain and then be meaningfully expressed or presented.

In an embodiment of the present invention, the radiological prose text definition ontology is constructed using combinations of one or more of the following World Wide Web Consortium standards:

RDF—Resource Description Framework
RDFS—RDF Schema
OWLDL—Web Ontology Language Description Logic version The radiological prose text definition ontology is utilized to define a plurality of specific concept ontology, which along with other report concepts, may then be utilized to construct a radiological prose text definition ontology.

Although the following discussions and the present invention are described in relation to a biological imaging report system, it should be understood that the invention is also applicable to other information/imaging technologies, systems or reports.

Ontology is a philosophy of what exists. In computer science, ontology is used to model entities of the real world and the relations between them to create common dictionaries for their discussion. Basic concepts of ontology include: 1) classes of instances/things; and 2) relations between the classes, as described below. Ontology provides a vocabulary for talking about things that exist.

Relations, also referred to as properties, attributes, and functions are specific associations of things with other things.

Imaging systems as discussed herein include those wherein image manipulation, image attributes, and features of an imaging system are required to be intuitively and easily analyzed and/or reported, including non-medical systems, visual analysis and diagnostic tools, and other visual user interface environments. Aside from the exemplary environment described herein, the system and method of the present invention is equally applicable to reporting or prose text generation in other fields, radiological environments, domains and for other imaging modalities. The use in other applications or by other systems or tools are anticipated and within the scope of the present invention.

In an embodiment of the present invention, a prose text definition ontology 100 that both declares and fulfills a model of radiological domain knowledge and linguistic formatting knowledge may be described as shown in FIG. 1.

Referring initially to FIG. 1, pathological, physiological and iatrogenic entities and pathological, physiological and iatrogenic observations may be modeled as radiological concepts. Concepts, concept instances, or properties may be expressed by a vocabulary that is defined in a radiological domain as radiological knowledge. Therefore, in connection with a particular image that is being observed or considered by a radiologist, various aspects of the image may be described by incomplete expressions or described merely as concepts and relationships.

Prose text definition ontology 100 may comprise a layered linguistic formatting ontology 102 and a radiological reporting domain ontology 104. The prose text definition ontology 100 may also be a single ontology that contains both the radiological domain knowledge and the knowledge of linguistic formatting. Alternatively, the prose text definition ontology 100 may be a layered ontology as presented herein. In an embodiment of the present invention, the radiological reporting domain ontology 104 is language independent and is provided as a base ontology. The radiological reporting domain ontology 104 may comprise concepts (classes) 106A, 106B, 106C, properties 108A, 108B and other objects 110. As previously mentioned, concepts 106A, 106B, 106C, properties 108A, 108B and other objects 110, would represent a radiological knowledge domain, which could be used to describe informational items that pertain to a patient, image, etc. The concepts 106A, 106B, 106C may themselves be defined by one or more ontology.

The layered linguistic formatting ontology 102 may be characterized by linguistic knowledge such as: language reference 111; a language tag 112; linguistic connectors 114A, 114B; sequences 116A, 116B; and definitions for various sections of a text report namely, report definition 118, section definition 120, paragraph definition 122 and sentence definition 124.

The language reference 111 provides a reference to an ontology that defines the language independent model and supplies the domain concepts, properties, and instances that are utilized by the prose text definition ontology 100. In the illustrated example, the language reference 111 would therefore provide references to the radiological reporting domain ontology 104. The language tag 112 may identify one or more languages that the linguistic formatting ontology 102 fulfills, i.e., the languages supported by the prose text definition ontology 100. The linguistic connectors 114A, 114B model adjacent linguistic relations that connect definitions within the radiological reporting domain ontology 104, i.e., the concepts 106, properties 108, and other objects 110. For example, and as illustrated in FIG. 1, connector 114A models the connection between Class A 106A and Property 1 108A. Similarly connector 114B illustrates that there is a connection between Class B 106B and Property 1 108A. This information is used to build or assemble the prose text and will be described later in this document. The sequence 116A models extensive linguistic relations that connect the definitions of the reporting domain ontology 104. For example, sequence 116B conveys a relative position relation for concepts 106B and 106C.

Extensive linguistic relations generally specify relative positioning of report domain knowledge in prose text. These relations are usually specified as declarations for a given concept and/or relationship. Such linguistic relations or sequences include:

1. Before/Precede relation—Models the prose text expression of a report domain ontology definition 1 that must be printed preceding the prose text expression of a report domain ontology definition 2 in the resulting prose text.
2. After/Follow relation—Models the prose text expression of a report domain ontology definition 1 that must be printed following the prose text expression of a report domain ontology definition 2 in the resulting prose text.
3. Order relation—Models the order of appearance when prose text expressions of multiple report domain ontology definitions occur simultaneously in the resulting prose text.
4. Conditions relation—Models the conditions that may affect any of the sequences.

The definitions 118, 120, 122, 124 for the various sections of a text report may be utilized to specify how each section would start and/or end. For example, report definition 118 may have an open block and a close block. The open block models the way a report starts, while the close block models how the report closes. Similarly, sentence definition 124, which could be considered a linguistic unit, may have an open block that models how a sentence should begin and a close block that models how a sentence should end.

When a study or other informational items pertaining to a patient is to be reported, the concepts 106A, 106B, 106C and properties 108A, 108B along with their relationships are converted to prose text by the layered linguistic formatting ontology 102. The linguistic formatting ontology 102 employs the concepts and their relations.

The present invention builds upon the fact that attributes within the realm of radiological knowledge (including diagnosis, anatomic location, and follow-up recommendation of pathological, physiological, and iatrogenic entities) and pathological, physiological, and iatrogenic observations may be modeled conceptually as radiological ontology to provide validation, identification and classification of radiological report information. The radiological report information may then be arranged and expressed as prose text. Importantly, the present invention utilizes an ontological model to build such prose text and is operable to import other ontology as needed. By utilizing ontology, the present invention is able to first consider what is specified by a piece of data before a sentence is structured using the data. In other words, the present invention is not simply rule based with a series of conditional inquiries, i.e., if/then statements. In operation, a relevant knowledge domain ontology is first consulted to obtain valid concepts and relationships, then the linguistic ontology is consulted to provide context and structure to express the concepts and relationships as prose text. This aspect is illustrated in FIG. 2.

Figure 2:
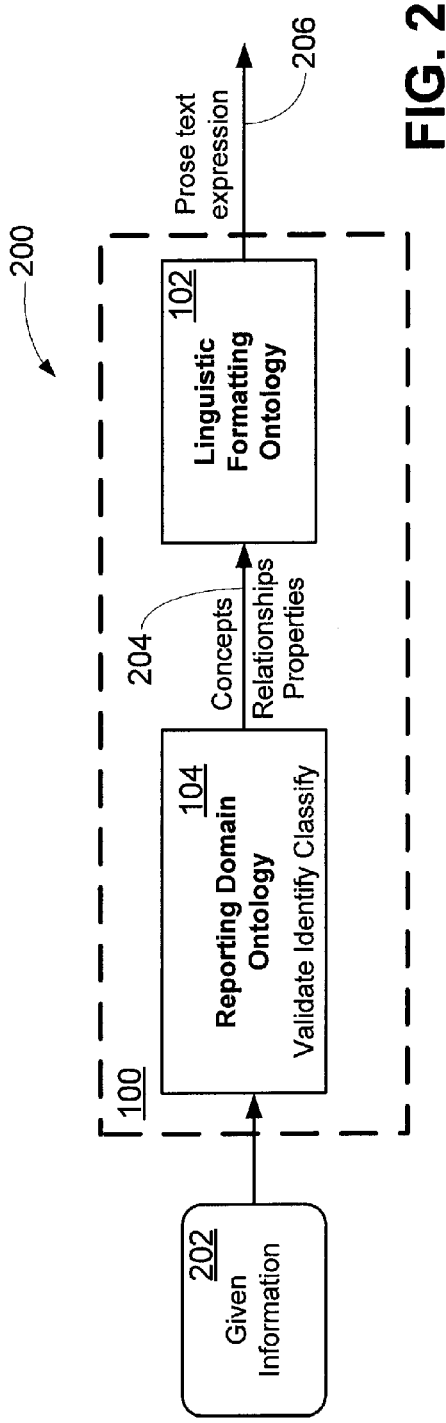
FIG. 2 is an illustrative diagram of an exemplary data flow according to the present invention.

FIG. 2 provides a data flow 200 that illustrates the sequence of operation and data flow of an embodiment of the present invention. Information items 202, which may originate from spoken words, an application program, other sources of information pertaining to a patient, or observations of a radiological image, etc., are provided to the prose text definition ontology 100. In operation, the information items 202 are presented in a consultation request to the radiological reporting domain ontology 104. As previously described, the information items 202 would then be validated, identified and classified to provide a model and representation of concepts having properties and relationships 204. The concepts, properties and relationships 204 are presented in another consultation to the linguistic formatting ontology 102, resulting in prose text 206. Prose text 206 expresses the concepts, properties and relationships 204 as sentences, paragraphs, sections or a complete report, as appropriate. The format or structure of the resulting prose text 206 is a function of the semantics defined by the linguistic knowledge of the system of the present invention and the modeled linguistic formatting ontology 102.

As previously mentioned, there are different linguistic connectors defined in the linguistic formatting ontology 102. In an embodiment of the present invention, each linguistic connector connects a class/property of a reference domain ontology to another class/property of the reference domain ontology. By definition, when two classes/properties are linked by a linguistic connector, nothing else can be inserted in-between the instances of the two classes/properties in the printed prose text except a prose text label of the specific linguistic connector. To illustrate this, an exemplary operation and representation 300 utilizing a linguistic connector in the manner described is presented in FIG. 3.

Figure 3:
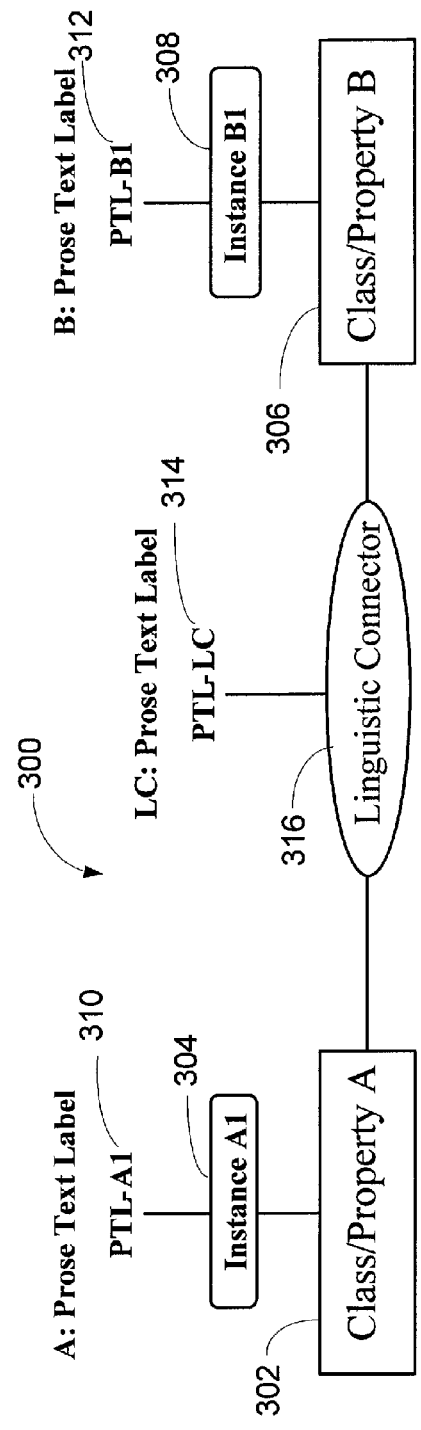
FIG. 3 is a representative diagram of a linguistic connector.

Turning to FIG. 3, class/property A 302 has an instance A1 304. Class/property B 306 has an instance B1 308. Class/property A 302 and class/property B 306 have a linguistic relation that is modeled by linguistic connector 316. Instance A1 304 is represented by prose text label PTL-A1 310, instance B1 308 is represented by prose text label PTL-B1 312, and linguistic connector 316 is represented by prose text label PTL-LC 314. According to the defined linguistic formatting ontology 102 of the present invention and as described earlier, the prose text presentation of the illustrated relation between the instances 304, 308, i.e., the printed prose text, would ordinarily be represented as:

A1 B1

However, due to the presence of the linguistic connector 316 and because a prose text label 314 is specified, the sequence of the printed prose text that is defined by the semantics of the linguistic format would be represented as:

A1 PTL-LC B1

Different presentations of the prose text may be specified by using other linguistic connectors such as special unary connectors.

Figure 4:
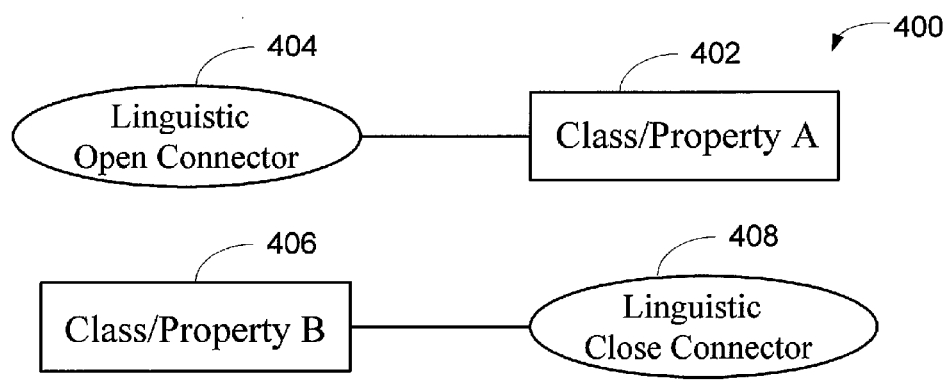
FIG. 4 is a representative diagram of unary linguistic connectors.

FIG. 4 illustrates the use of special unary linguistic connectors that can be applied to produce the starting or ending prose text of a sentence, paragraph, or section in a prose text report. As shown, a class/property A 402 is associated with a linguistic open connector 404 for specifying the starting prose text. In one embodiment of the present invention, the label of linguistic open connector 404 provides the starting text, in a manner similar to the earlier described representation of the linguistic connector 316. In an alternate embodiment, the linguistic open connector 404 specifies that an instance of the class/property would be the starting text. In either case 404 may also specify what class or property A 402 follows the open connector.

A class/property 406 is also shown with a linguistic close connector 408. In this case, the close connector 408 provides or specifies the ending prose text as the label of the connector or the instance of the class/property B 406, depending on the embodiment of the invention.

Figure 5:
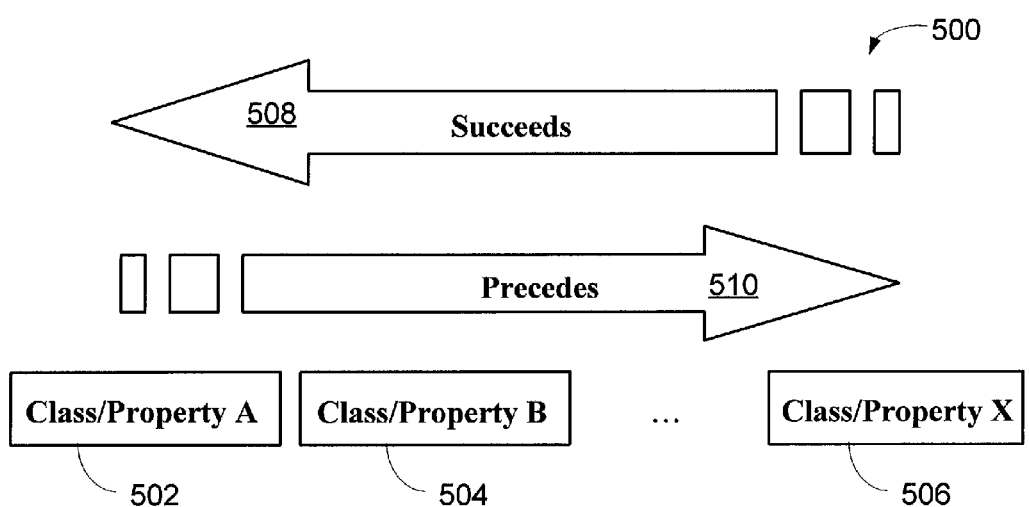
FIG. 5 is a block diagram illustrating the linguistic declarations of succeeds and precedes.

Turning next to FIG. 5, the precedes and succeeds declarations of the linguistic knowledge are described with reference to the illustrated diagram 500. Unlike the connectors that were described earlier, the precedes/succeeds declarations specify only the loose relative relations between two classes/properties. There may be zero to an unlimited number of other instances existing between the classes/properties that have been specified in this type of relationship. As such, the declaration generally combines with an order declaration to provide the format of a prose text template. The sequence for concept A 502, concept B 504 and concept X 506 may be declared by a succeeds 508 or precedes 510 declaration. Hence, providing a relative position for each these concepts 502, 504, 506. However, the declarations 508, 510 do not limit or address other instances that may exist between the concepts 502, 504, 506. Even further, the declarations 508, 510 do not provide a specification of which instance should be printed first. So for example, if concept B 504 is declared to precede concept X 506, and concept A 502 is declared to precede concept X 506, then either of the concepts (i.e., concept A 502 or concept B 504) may be interjected between the other and the concept X 506. In other words, there is no limitation to the specific distance of the instances from each other or their sequence. A prose text expression for concept A 502 and concept B 504 may be presented in a sentence with any number of other texts between them. Additionally, concept B 504 may be printed before concept A 502 or vice versa, as long as they are both printed before concept X 506. In certain circumstances, this scenario will not do. This is particularly the case when the objective is to provide meaningful and/or grammatically correct prose text expressions. As such, an order declaration may be required in certain instances to address relative positions.

Figure 6:
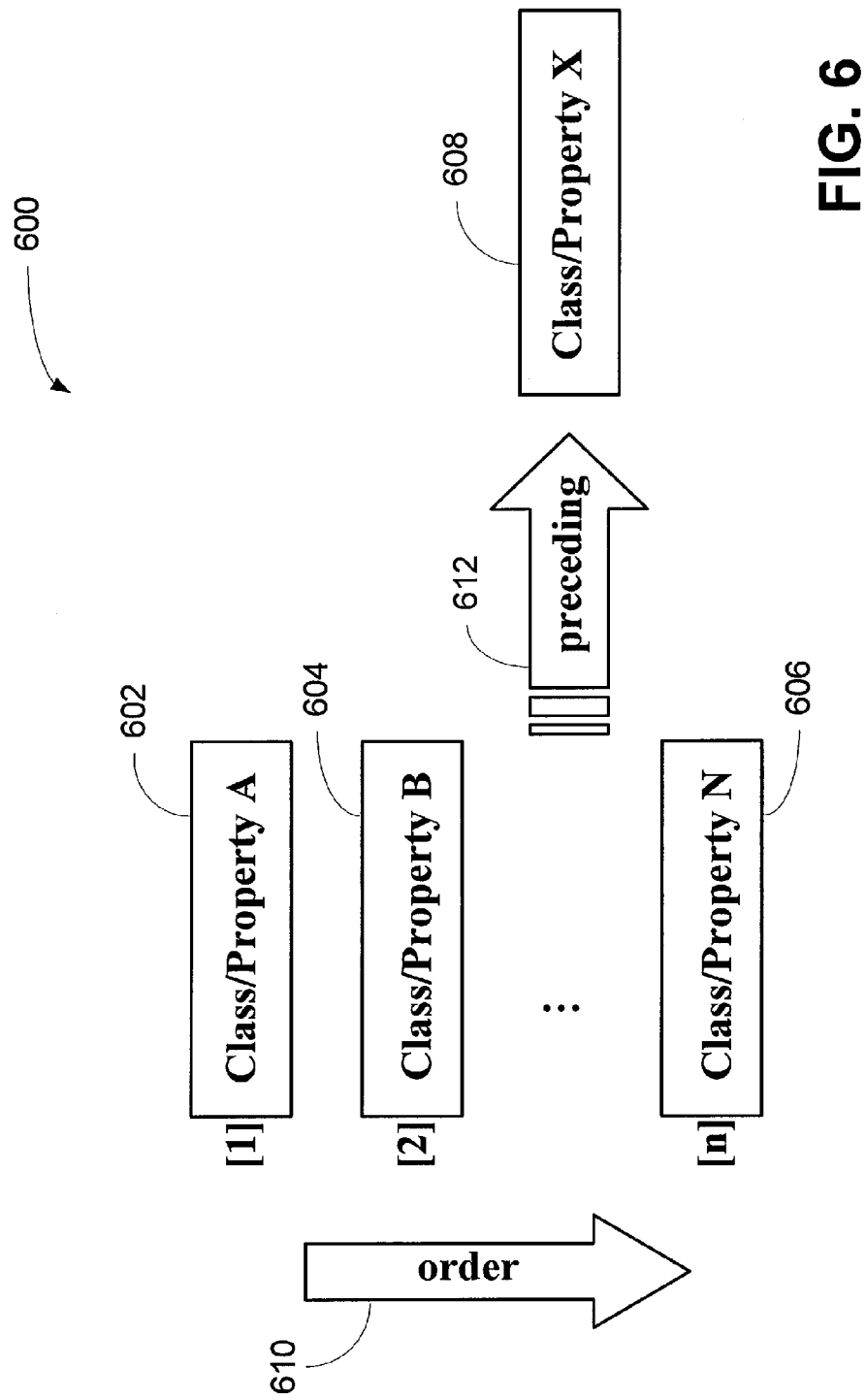
FIG. 6 is a diagram illustrating the relative position of objects as a function of linguistic declarations.

FIG. 6 provides a block diagram 600 that illustrates the combination of an order declaration with precede/succeed declarations. An order declaration defines relative positions between two instances. The difference between precede/succeed and order relations is the unconditional sequence vs. the conditional sequence. When A precedes B, in any situation A precedes B. When A has a higher order in the sequence of printing than B has, the order is under a certain condition, e.g., when both of them precede X. Turning to the block diagram 600, if class/property A 602, class property B 604 and class/property N 606 are declared to precede class/property X 608, without more, it would be unclear which of the preceding group of class/properties 602, 604, 606 would be printed first. This quandary is resolved by the declaration of an order 610. As shown, given the order 610, all of the displayed class/properties 602, 604, 606, 608 would be printed in the following sequence: class/property A 602 first, then class/property B 604, then all other instances through class/property N 606, followed finally by class/property X 608.

In order to facilitate reference and identification of the parts of a radiological image for the purpose of diagnosis or analysis of a subject, the various parts of the image may need to be reported upon. The present invention provides a system and method for consulting the prose text definition ontology 100 for providing validation, identification and classification of the report information and ultimately prose text expression of the consultation in a particular language. As previously mentioned, the prose text definition ontology 100 provides support for multiple languages specified in the language tags 112, via the linguistic formatting ontology 102 through a language independent radiological reporting domain ontology 104. This feature is described with reference to FIG. 7.

Figure 7:
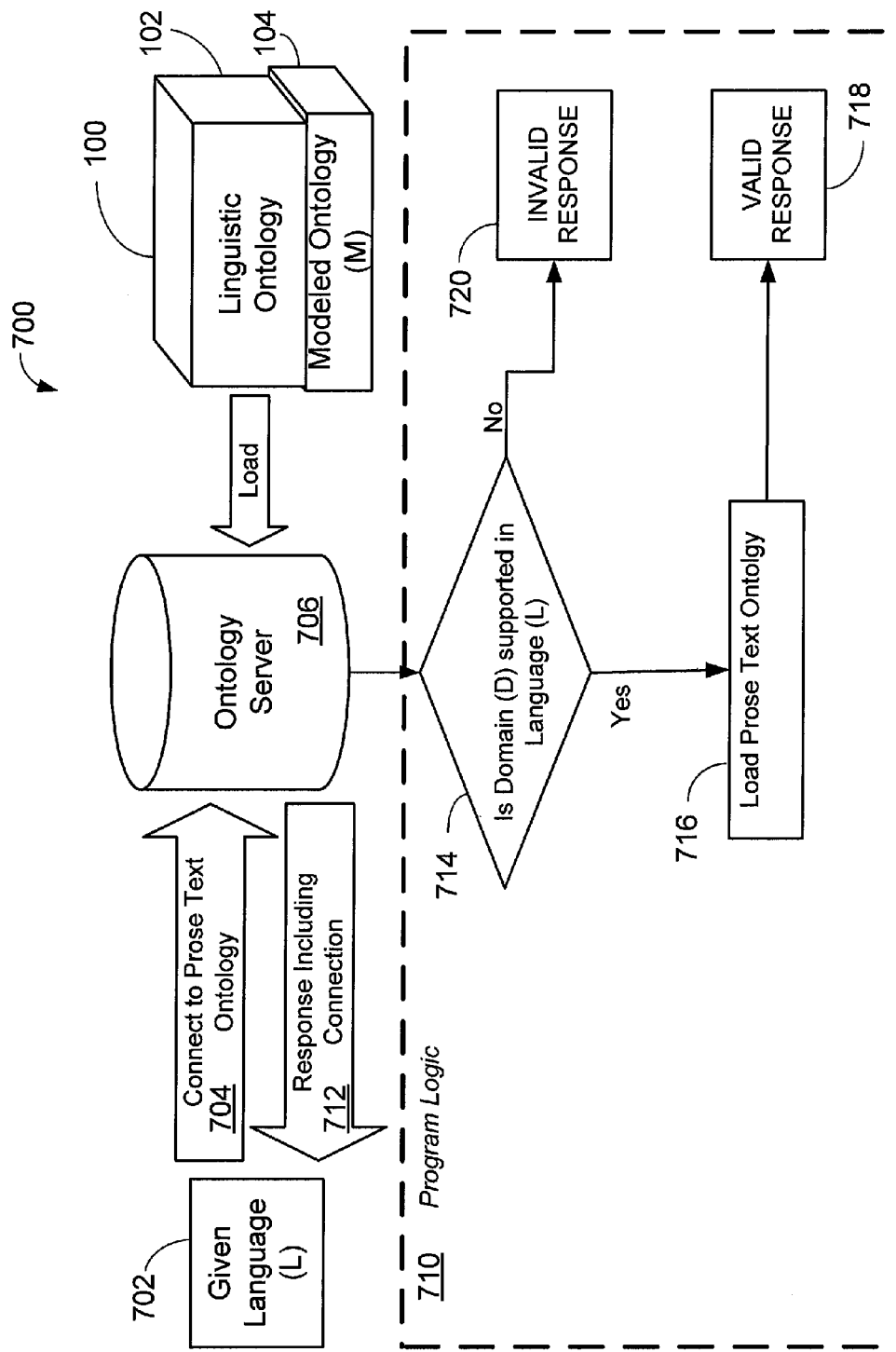
FIG. 7 is a data and flow illustration for determining support for a given language L in the prose text definition ontology of FIG. 1.

As illustrated in FIG. 7, an application program or other source having a given one or more languages L 702 that is to be utilized for reporting, initiates a connection request 704 in a specific one or more languages L to an ontology server 706. The ontology server 706 is loaded with the prose text definition ontology 100. As previously described, prose text definition ontology 100 comprises the linguistic formatting ontology 102 and the modeled radiological reporting domain ontology M 104. Program logic 710 accepts the connection request 704 and provides a connection response 712. Program logic 710 may reside on the ontology server 706 or reside on another device having access to the ontology server 706. In operation, program logic 710 determines at step 714, if the requested one or more connection languages L 702 are supported by the prose text definition ontology 100. For each language L 702 that is supported, the linguistic formatting ontology 102 for the language L 702 is loaded at step 716. A valid response indication 718 is then provided in the connection response 712. The modeled radiological reporting domain ontology M 104 may be automatically loaded following, prior to, or contemporaneous with step 716. Identification of a definitive concept that resides in the radiological reporting domain 104 may thus be determined. In the event that the given one or more languages L 702, is not supported by the prose text definition ontology 100, as determined at step 714, an invalid response indication 720 is provided in the connect response 712.

Figure 8:
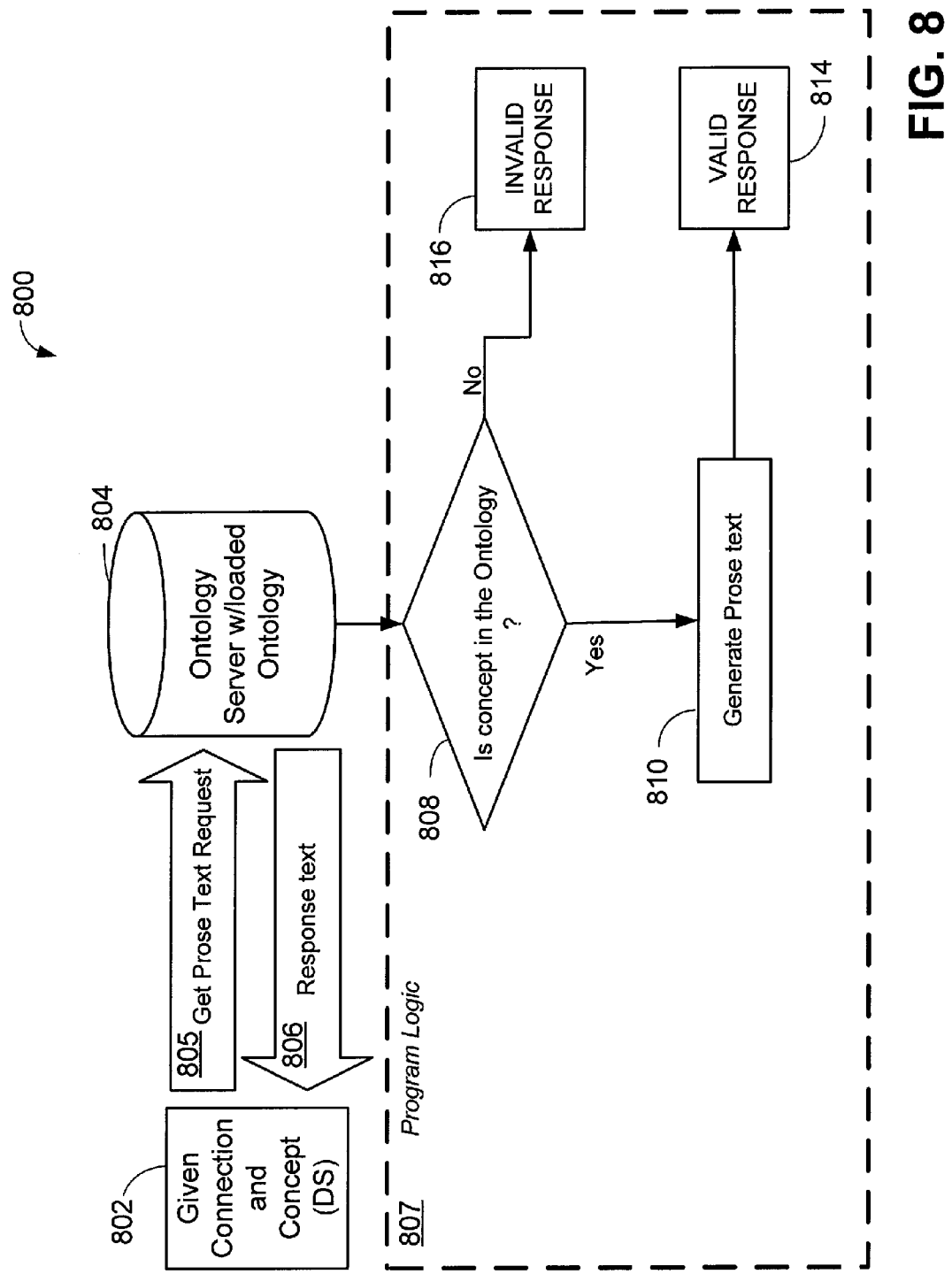
FIG. 8 is a data and flow illustration for providing prose text for a given connection and concept to be reported.

Generally, the present invention consults the prose text definition ontology 100 with a particular knowledge concept to provide a resulting prose text. FIG. 8 illustrates the operation of this aspect of the invention. Having a given connection and concept DS 802, which is to be reported, the system of the present invention initiates a prose text request 805 to an ontology server 804. The ontology server 804 has the prose text definition ontology 100 of FIG. 1 loaded thereon. Program logic 807 accepts the prose text request 805 and provides a response text 806. Program logic 807 may reside on the ontology server 804 as shown or reside on another device having access to the ontology server 804. In operation, program logic 807 determines at step 808, if the given concept DS 802 is valid in the modeled prose text definition ontology 100. If the given concept DS 802 is deemed valid, then a prose text that resides in the domain is determined at step 810. Following this, a valid response indication 814, is provided in the response text 806. In the event that the given concept DS 802 is not a valid linguistic information item within the prose text definition ontology 100 as determined at step 808, an invalid response indication 816 is provided in the response text 806.

In an even further aspect, the present invention provides translation for a given concept through a consulting connection to the prose text definition ontology 100. This aspect is best described with reference to the illustration of FIG. 9. Having a given connection and concept DS 902 that is to be translated, the system of the present invention initiates a translation request 904 to the ontology server 804. The ontology server 804 is loaded with prose text definition ontology 100. Program logic 907, which may reside on the ontology server 804 as shown, or reside on another device having access to the ontology server 804, accepts the translation request 904 and provides a response text 906. In operation, program logic 907 determines at step 908, if the given language and concept DS 902 is valid in the modeled prose text definition ontology 100. If this condition is satisfied, translation text is provided at step 910. Following this, a valid response indication 914, is provided in the response text 906. In the event that the given concept DS 902 is not valid linguistic information within the prose text definition ontology 100 as determined at step 908, an invalid response indication 912, is provided in the response text 906.

Figure 9:
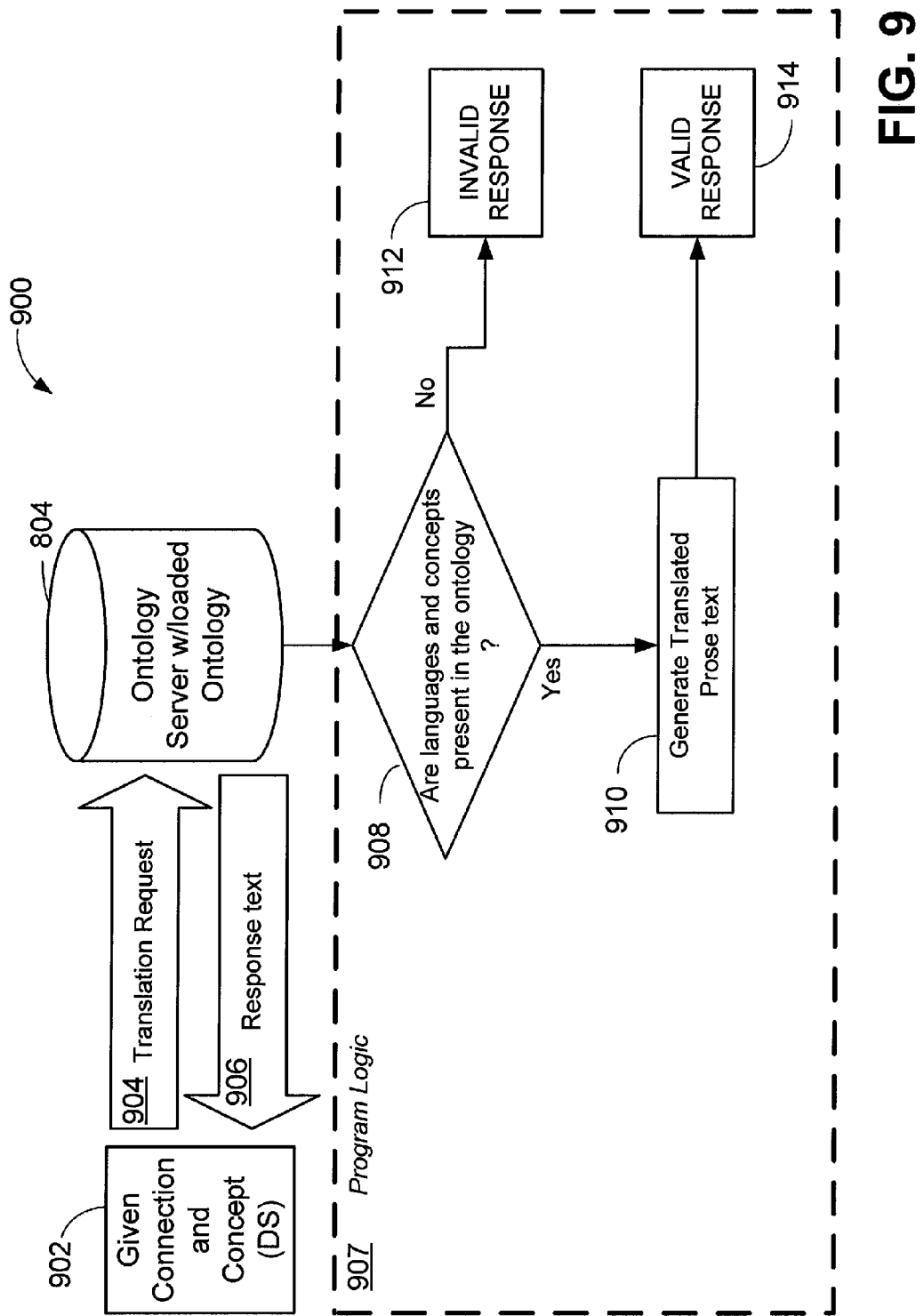
FIG. 9 is a data and flow illustration for providing translated prose text according to the present invention.

In either of the inventive aspects described respecting obtaining prose text in FIG. 8 or obtaining translated prose text in FIG. 9, it should be understood that the present invention provides features to enable the addition of new concepts to the prose text definition ontology 100 when concepts are found to be non-existent. In other words, the system has the ability to learn and grow the linguistic knowledge domain.

To further illustrate an application of the various features and aspects of the invention, an implementation example of the above described invention is next described. In this implementation example, a radiological ontology for mammography is utilized. An application program obtains mammographic radiological domain ontology information describing a mammographic radiological finding and it mammographic radiological finding characteristics.

Initially, the system and method of the present invention models the mammographic information in the manner described earlier in this document. That is to say that the knowledge of the mammography ontology is modeled as concepts, object properties/relationships, and constraints on the concepts including those contained in one or more imported ontology. Concept properties are thus defined for a report domain ontology. A linguistic formatting ontology for supported languages with appropriate references to the mammography ontology is then modeled. This combined ontology is referred to as mammography prose text definition ontology.

Next a system and method are provided for consulting the combined ontology as independent software that can be utilized by other software or systems. Using the system and methods described herein, an application program obtains a connection to the mammography prose text definition ontology in the desired language. The application consults the mammography prose text definition ontology to determine the correct way to express the mammography finding and finding characteristics. The mammography prose text definition ontology system may then respond with the correct prose text for that specific mammographic finding having those specific characteristics.

As previously explained, using the system and methods described herein, the reporting application consults the mammography report domain ontology portion of the mammography prose text definition ontology about each piece of purported mammographic radiological report information to validate that the information belongs to the mammography radiological report information domain. The application also receives the identity of the information and the classification for the sought after information.

The application examines the classification of each piece of information and if one informational item is classified as a mammography radiological concept, then the mammography report domain ontology is consulted in the context of the mammography radiological concept, and any relevant constraints or relationships are explored to validate the concept, i.e., determine whether the radiological report concepts apply to the radiological report currently in consideration.

These steps result in providing radiological report information that has been validated, identified and classified in the mammography report domain ontology, before it is presented to the linguistic formatting ontology. The linguistic formatting ontology in turn presents prose text to express the mammographic information.

While the preceding implementation and the present invention are described in the domain of mammography, the present invention is applicable to any report domain ontology in the field of radiology.

Having described the system and method of the present invention and an embodiment thereof, an exemplary computer environment for implementing the described design and execution is presented next.

Figure 10:
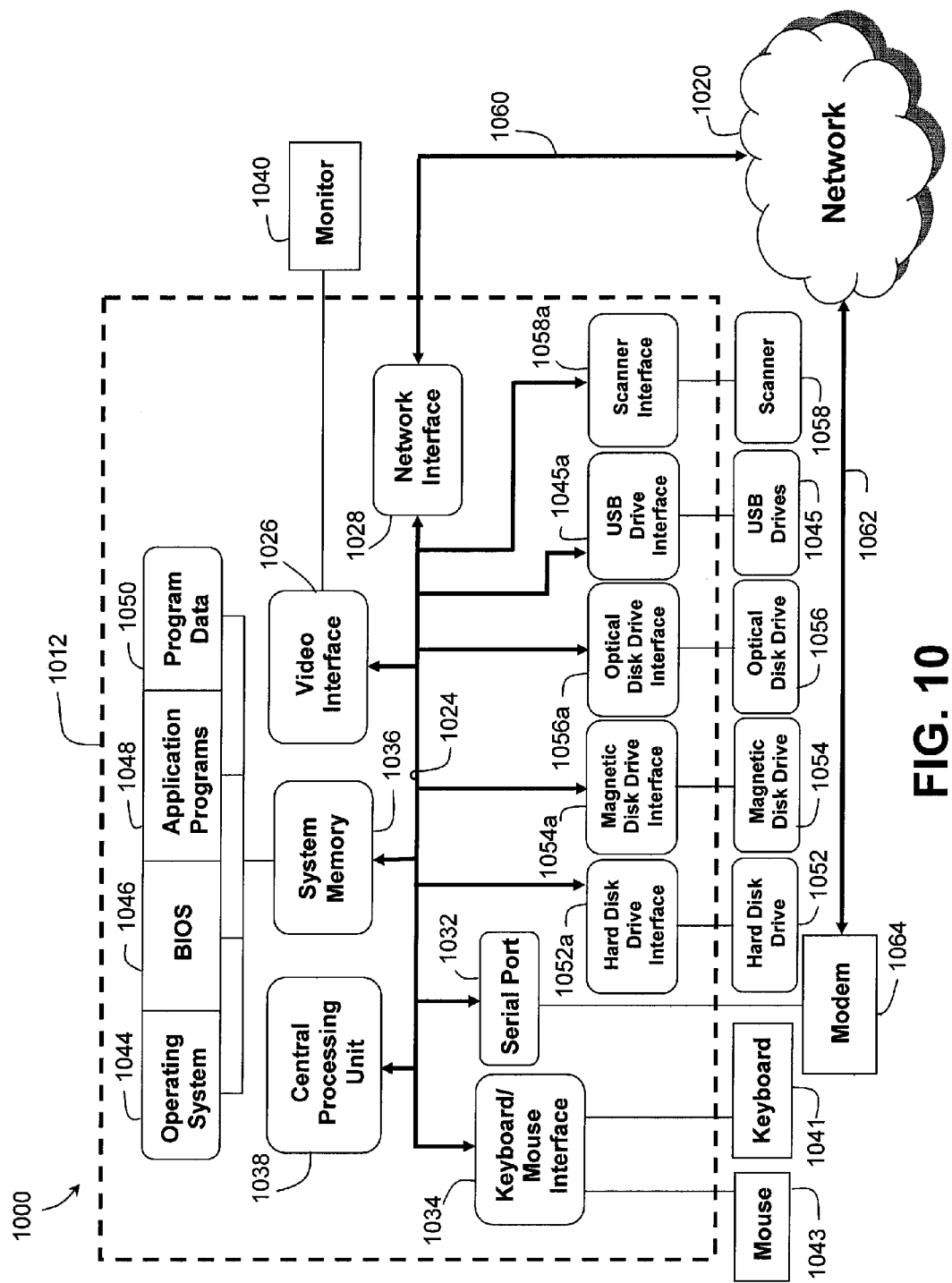
FIG. 10 is a block diagram generally illustrating a computing environment in which the invention may be implemented.

FIG. 10 shows an exemplary computing environment 1000 that can be used to implement through programming, any of the processing thus far described. The computing environment may comprise a computer 1012 including a system bus 1024 that couples a video interface 1026, network interface 1028, one or more serial ports 1032, a keyboard/mouse interface 1034, and a system memory 1036 to a Central Processing Unit (CPU) 1038. Computer 1012 may also include a Graphics Processing Unit (GPU) or one or more other special or general purpose processing units. A monitor or display 1040 is connected to bus 1024 by video interface 1026 and provides the user with a graphical user interface to view, edit, and otherwise manipulate digital images. The graphical user interface allows the user to enter commands and information into computer 1012 using a keyboard 1041 and a user interface selection device 1043, such as a mouse or other pointing device. Keyboard 1041 and user interface selection device are connected to bus 1024 through keyboard/mouse interface 1034. The display 1040 and user interface selection device 1043 are used in combination to form the graphical user interface which allows the user to implement at least a portion of the present invention. Other peripheral devices may be connected to computer 1012 through serial port 1032 or universal serial bus (USB) drives 1045 to transfer information to and from computer 1012. For example, CT scanners, X-ray devices and the like may be connected to computer 1012 through serial port 1032 or USB drives 1045 so that data representative of a digitally represented still image or video may be downloaded to system memory 1036 or another memory storage device associated with computer 1012 to enable processes and functions in accordance with the present invention.

The system memory 1036 is also connected to bus 1024 and may include read only memory (ROM), random access memory (RAM), an operating system 1044, a basic input/output system (BIOS) 1046, application programs 1048, and program data 1050. The computer 1012 may further include a hard disk drive 1052 for reading from and writing to a hard disk, a magnetic disk drive 1054 for reading from and writing to a removable magnetic disk (e.g., floppy disk), and an optical disk drive 1056 for reading from and writing to a removable optical disk (e.g., CD ROM or other optical media). The computer 1012 may also include USB drives 1045 and other types of drives for reading from and writing to flash memory devices (e.g., compact flash, memory stick/PRO and DUO, SD card, multimedia card, smart media card), and a scanner 1058 for scanning items such as digital images to be downloaded to computer 1012. A hard disk interface 1052a, magnetic disk drive interface 1054a, a optical drive interface 1056a, a USB drive interface 1045a, and a scanner interface 1058a operate to connect bus 1024 to hard disk drive 1052, magnetic disk drive 1054, optical disk drive 1056, USB drive 1045 and a scanner 1058, respectively. Each of these drive components and their associated computer-readable media may provide computer 1012 with non-volatile storage of computer-readable instruction, program modules, data structures, application programs, an operating system, and other data for the computer 1012. In addition, it will be understood that computer 1012 may also utilize other types of computer-readable media in addition to those types set forth herein, such as digital video disks, random access memory, read only memory, other types of flash memory cards, magnetic cassettes, and the like.

Computer 1012 may operate in a networked environment using logical connections with image capture devices such as MRI, CT scanners, Ultrasound, Positron Emission Tomography (PET) or X-Ray devices. Network interface 1028 provides a communication path 1060 between bus 1024 and network 1020, which allows images to be communicated through network 1020 from any of the previously identified imaging devices, and optionally saved in a memory, to the computer 1012. This type of logical network connection is commonly used in conjunction with a local area network. Images may also be communicated from bus 1024 through a communication path 1062 to network 1020 using serial port 1032 and a modem 1064. Using a modem connection between the computer 1012 and imaging devices may be used in conjunction with a wide area network or the Internet. It will be appreciated that the network connections shown herein are merely exemplary, and it is within the scope of the present invention to use other types of network connections between computer 1012 and imaging devices including both wired and wireless connections.

The present invention provides a useful, novel and non-obvious means to utilize radiological report domain ontology to validate, identify, and classify radiological information for reports and utilize linguistic layer ontology to provide prose text expressions of the radiological report information. In other words, the present invention provides means to determine what informational items are allowable and/or belong in a given report and how to best express them.

Additionally, the present invention provides a tool that may be utilized by other applications or systems as a building block for further information processing.

From the foregoing, it will be seen that this invention is one well adapted to attain all the ends and objectives hereinabove set forth together with other advantages which are obvious and which are inherent to the method and apparatus. It will be understood that certain features and sub-combinations are of utility and may be employed without reference to other features and sub-combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. As used herein, the terms "having" and/or "including" and other terms of inclusion are terms indicative of inclusion rather than requirement.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed, as the best mode contemplated for carrying out this invention, but that the invention will include all embodiments falling within the scope and spirit of the appended claims.

What is claimed is:

1. A method programmed for execution in a computing device for providing prose text report generation from a patient consultation, the method comprising:

capturing two or more orally provided knowledge information items pertaining to a patient or observations of a radiological image during the patient consultation, said two or more orally provided knowledge information items being provided in a memory of the computing device; and utilizing a prose text definition ontology having linguistic knowledge and a base report domain ontology to structure one or more sentences of a prose text report based on said knowledge information items for presentation to a user;

said prose text definition ontology comprising:

one or more references to said base report domain ontology;

one or more connectors for modeling adjacent linguistic relations to connect concepts from said base report domain ontology; and one or more sequences for modeling relations among concepts from said base report domain ontology;

wherein said prose text definition ontology is consulted with concepts from said base report domain ontology to provide prose text that expresses said concepts and relationships involved in the patient consultation;

wherein said base report domain ontology imports said knowledge items pertaining to the patient, defines said knowledge items as report domain concepts of said base report domain ontology, identifies relationships between said report domain concepts, and identifies constraints on said report domain concepts, wherein said knowledge items are identified, classified and validated in the context of said base report domain ontology; and wherein said report domain concepts, said relationships between said report domain concepts and said constraints on said report domain concepts are presented to said prose text definition ontology to be expressed as prose text using said references, said connectors and said sequences in said one or more sentences.

2. A method programmed for execution in a computing device for consulting and creating a prose text report from a radiological domain ontology in reference to a subject, the method comprising:

defining one or more aspects of radiology report information as concept properties represented by a vocabulary of one or more instances of said radiological domain ontology, said radiological domain ontology declaring and fulfilling a model of radiological domain knowledge;

acquiring an orally provided non-radiological information item of interest that relates to said subject, said non-radiological information item of interest being provided to a memory of the computing device;

employing a context that defines a set of said radiological domain knowledge and the relationships among said set of radiological domain knowledge to describe said subject;

validating that said information item of interest is reportable radiological information and resides in said set of radiological domain knowledge;

identifying a definitive concept of said information item of interest from within said set of radiological domain knowledge;

classifying said informational item of interest; and employing a context that defines a set of linguistic knowledge and the relationship among said set of linguistic knowledge to express said concept properties;

wherein said concept properties are expressed in the context of a linguistic ontology as prose text in the created prose text report.

3. The method of claim 2 wherein said set of linguistic knowledge comprises:

references to said radiological domain ontology;

connectors for modeling adjacent linguistic relations that connect concepts within said radiological domain ontology; and sequences for modeling relations among concepts within said radiological domain ontology.

4. The method of claim 3, wherein said set of linguistic knowledge further comprises:

an open block for modeling the way the prose text report or a linguistic unit in the prose text starts; and a close block for modeling the way the prose text report or a linguistic unit in the prose text ends.

5. The method of claim 2 further comprising providing a set of sub-ontologies to said set of linguistic knowledge, wherein each of said sub-ontologies is dedicated to a specific language or dialect.

* * * * *